United States Patent [19]

Nagatsu et al.

[11] Patent Number: 4,900,826
[45] Date of Patent: Feb. 13, 1990

[54] PROCESS FOR PREPARING N6,9-DISUBSTITUTED ADENINE

[75] Inventors: Yoshiro Nagatsu; Hideo Isozaki; Tooru Shiroshita; Jiro Suzuki, all of Yatsushiro, Japan

[73] Assignee: Kohjin Co., Ltd., Tokyo, Japan

[21] Appl. No.: 419,317

[22] Filed: Sep. 17, 1982

[30] Foreign Application Priority Data

Sep. 24, 1981 [JP] Japan ................. 56-149567
Sep. 30, 1981 [JP] Japan ................. 56-153878
Oct. 1, 1981 [JP] Japan ................. 56-154862

[51] Int. Cl.$^4$ ........................... C07D 473/34
[52] U.S. Cl. .................................. 544/277
[58] Field of Search ........................ 544/277

[56] References Cited

U.S. PATENT DOCUMENTS 4,100,159  7/1978  Zwan .................. 544/277
4,174,440  10/1979  Shinkai et al. ....... 544/277
4,189,485  2/1980  Matsuno et al. ...... 544/277

OTHER PUBLICATIONS

Melvin Sutherland et al., J. Am. Chem. Soc., vol. 79, pp. 2251–2252 (1957).
Starks et al., *Phase Transfer-Catalyst*, Principles and Techniques 1978, Academic Press, New York, pp. 1–12, 58–59, 77–82 112–117 and 217–223.
Starks, "Chemtech", 1980, pp. 110–117.
Ford, "Chemtech", 1984, pp. 436–439.

*Primary Examiner*—Glennon H. Hollrah
*Assistant Examiner*—James H. Turnipseed
*Attorney, Agent, or Firm*—Armstrong, Nikaido Marmelstein, Kubovcik & Murray

[57] ABSTRACT

A process for preparing $N^6$, 9-disubstituted adenines which comprises reacting a metal salt of $N^6$-substituted adenine with a benzyl halide compound, preferably in the presence of a phase transfer catalyst. According to the process, the $N^6$,9-disubstuted adenines can be obtained in high yields and good selectivity.

9 Claims, No Drawings

PROCESS FOR PREPARING N6,9-DISUBSTITUTED ADENINE

BACKGROUND OF THE INVENTION

The present invention relates to a process for preparing N6,9-disubstituted adenines, and more particularly to a process for preparing N6,9disubstituted adenines in high yields and good selectivity by the alkylation of metal salts of N6-substituted adenines with substituted benzyl halide.

Known processes for preparing N6,9-disubstituted adenines are hard to adopt to the industrial production, because of complication of process steps or use of expensive raw materials. Among them, a process as disclosed in U.S. Pat. No. 4,189,485 attracts attention, because of its simple process. However, the yield of the product is low and is at most 60 %. Moreover, since the undesired 3-isomer is by-produced, it is expected that the yield of the desired 9-isomer is very low.

The N6,9-disubstituted adenines are compounds useful as plant growth regulators, antivirotics and anticoccidial agents, and in recent years, the use as anticoccidial agents has been particularly watched. In case that they are used as anticoccidial agents, it is necessary to control the incorporation of the 3-isomer by-produced generally upon alkylating adenine derivatives in alkaline mediums in as trace amounts as possible, i.e. below 100 p.p.m.

U.S. Pat. No. 4,171,440 discloses a process for the purification of 9-(2,6-dihalobenzyl)adenines which are similar compounds to the N6,9-disubstituted adenines. In this process, the undesired 3-isomer is removed by treating the 9-isomer containing the 3-isomer with concentrated sulfuric acid by utilizing the property of the 3-isomer based on the thermodynamic instability. This purification process has the disadvantages that the procedure is very complicated and the use of large quantities of concentrated sulfuric acid is necessary.

It is known that N6-substituted adenines used as intermediates in the process of the present invention are prepared by reacting 6-hydroxypurine with phosphorus oxychloride and reacting the resulting 6-chloropurine with a corresponding amine, as disclosed in Japanese Examined Patent Publication (Tokkyo Kokoku) No. 3319/1968, No. 6222/1968 and No. 27649/1969 and J. Am. Chem. Soc., Vol. 79, 2251(1957). These processes have the disadvantage of being unsuitable for industrialization, since the reactions are carried out in two steps and raw materials are expensive. For instance, in the preparation of 6-chloropurine from 6-hydroxypurine, expensive phosphorus oxychloride is used as a chlorinating agent, and also the yield thereof is not so high, i.e. 50 to 60 %. Further, the post-treatment of the reaction and the recovery of the product are difficult. Since anticoccidial agents are very inexpensive as compared with pharmaceuticals, it is required that intermediates used for the preparation of anticoccidial agents are very inexpensive.

It is an object of the present invention to provide a process for preparing N6,9-disubstituted adenines in high yields and high purities.

A further object of the invention is to provide a process for preparing N6,9-disubstituted adenines in high yields and high purities by the reaction of N6-substituted adenines with benzyl halide compounds.

Another object of the invention is to provide a process for preparing N6,9-disubstituted adenines from adenine through N6-substituted adenines.

A still another object of the invention is to provide a process for preparing pure N6,9-disubstituted adenines having a low content of impurities, N6,3-disubstituted adenines.

SUMMARY OF THE INVENTION

It has now been found that N6,9-disubstituted adenines can be prepared in high yields and high purities by reacting metal salts of N6-substituted adenines with benzyl halide compounds, especially in the presence of phase transfer catalyst.

In accordance with the present invention, there is provided a process for preparing a N6,9-disubstituted adenine having the general formula (I):

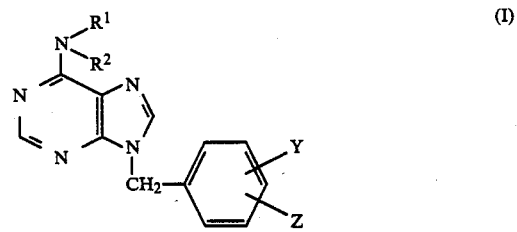

wherein $R^1$ is hydrogen, a lower alkyl group having 1 to 4 carbon atoms, benzyl group or fulfuryl group, $R^2$ is a lower alkyl group having 1 to 4 carbon atoms, benzyl group or fulfuryl group, Y and Z are the same or different and each is hydrogen, chlorine, bromine or fluorine, which comprises reacting a metal salt of N6-substituted adenine having the general formula (II):

wherein $R^1$ and $R^2$ are the same as defined above, M is an alkali metal or an alkaline earth metal and n is an integer of 1 or 2, with a benzyl halide compound having the general formula (III):

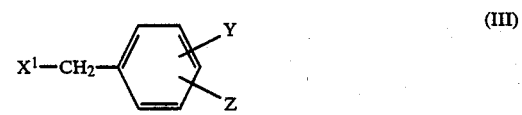

wherein Y and Z are the same as defined above, and $X^1$ is chlorine or bromine, preferably in the presence of a phase transfer catalyst.

It has also been found that a N6-substituted adenine having the general formula (IV):

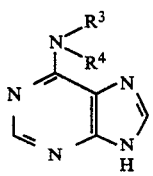
(IV)

wherein $R^3$ is hydrogen or a lower alkyl group having 1 to 4 carbon atoms, and $R^4$ is a lower alkyl group having 1 to 4 carbon atoms, which is used as an intermediate for the preparation of the $N^6$,9-disubstituted adenines having the general formula (I) can be inexpensively prepared in a high purity by reacting adenine with an aliphatic amine having the general formula (V):

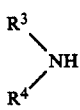
(V)

wherein $R^3$ and $R^4$ are the same as defined above, at elevated temperatures, preferably in the presence of a catalyst such as a hydrogen halide, a mineral acid, an organic sulfonic acid, a Lewis acid or a metal or metal salt capable of forming a complex ion with the aliphatic amine. Accordingly, the desired $N^6$,9-disubstituted adenines are prepared inexpensively in high yields and high purities by employing adenine as a starting material.

The reaction product obtained by the above-mentioned process is a mixture of a major amount of $N^6$,9-disubstituted adenines and a minor amount of $N^6$,3-disubstituted adenines. It has been found that when the reaction product is dissolved in glacial acetic acid at elevated temperatures and to the solution is added hot water, the desired 9-isomer is selectively precipitated. The desired $N^6$,9-disubstituted adenines of high purity are obtained from the reaction product by this purification process.

DETAILED DESCRIPTION

The process for preparing a $N^6$,9-disubstituted adenine of the general formula (I) in accordance with the present invention is characterized by the following points:

(1) A $N^6$-substituted adenine is reacted in the form of its metal salt with a benzyl halide compound.

(2) The reaction is preferably carried out in a solvent which substantially does not dissolve the metal salt of $N^6$-substituted adenine and readily dissolves the benzyl halide compound, in the presence of a phase transfer catalyst.

That is, it is possible to suppress the formation of the 3-isomer shown below and to increase the selectivity of the 9-isomer, i.e. the desired compound (I), by using the metal salt of $N^6$-substituted adenine given by the general formula (II) as a starting material. It is also possible to accelerate the main reaction with preventing side reactions, to increase the conversion and to much more improve the selectivity of the 9-isomer by coexisting the phase transfer catalyst in the reaction system.

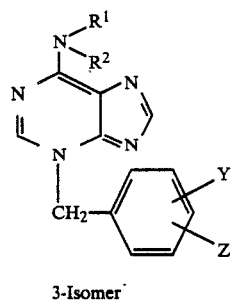

3-Isomer

Phase transfer catalysts generally used heretofore are quaternary ammonium salt, phosphonium salt and crown ether, all of which are expensive and can hardly be recovered for re-use. The quaternary ammonium salt, in particular, is unstable and can never be recovered. As a result of looking into some other phase transfer catalysts which may replace these catalysts, it has been found out that polyethylene glycol, diethylene glycol or their alkyl ether are particularly effective for the above reaction.

A similar reaction is shown in U.S. Pat. No. 4,100,159. This patent discloses a process for preparing 9-(dihalobenzyl)adenine by reacting a metal salt of adenine, with a dihalobenzyl halide in a solvent which substantially does not dissolve the metal salt of adenine but dissolves the dihalobenzyl halide in the presence of a phase transfer catalyst. The quaternary ammonium salt and phosphonium salt are the only phase transfer catalyst mentioned in the patent and no catalysts of polyethylene glycol type or diethylene glycol type are described in the patent.

The metal salt of $N^6$-substituted adenine given by the aforementioned general formula (II) includes the metal salts of $N^6$-substituted adenines such as $N^6$-methyl-, ethyl-, n-propyl-, n-butyl-, benzyl-, furfuryl-, dimethyl- and diethyl-adenines. The metal salts are alkali metal salts such as lithium, sodium and potassium salts, and alkaline earth metal salts such as magnesium, calcium and barium salts.

The metal salt of $N^6$-substituted adenine of the general formula (II) can be prepared by reacting a $N^6$-substituted adenine having the general formula (II'):

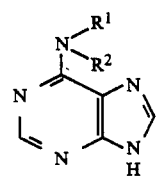
(II')

wherein $R^1$ and $R^2$ are the same as defined above, with a strongly basic compound of an alkali metal or an alkaline earth metal.

There is no particular limitation with respect to the process of converting the $N^6$-substituted adenine of the general formula (II') into its metal salt, but the easiest method is to dissolve the $N^6$-substituted adenine into an aqueous solution containing an amount of metal hydroxide equivalent to the $N^6$-substituted adenine, followed by the evaporation of the water under a reduced pressure. Another simple method is to mix the $N^6$-substituted adenine with a concentrated aqueous solution of metal hydroxide in a reaction solvent prior to the reaction and to use the obtained mixture as it is in the reaction. As a still another method, it is also possible to use metal hydride such as sodium hydride, metal alcoholate such as sodium methylate, and metal amide such as sodium amide.

The benzyl halide compound given by the aforementioned general formula (III) includes benzyl chloride, benzyl bromide, 2,6-dichlorobenzyl chloride, 2,6-dichlorobenzyl bromide, 2-chloro-6-fluorobenzyl chloride and 2-chloro-6-fluorobenzyl bromide, but is not limited to these compounds. As the amount of the benzyl halide compound used, the amount equivalent to $N^6$-substituted adenine is sufficient and there is no need to use it in excess. Unless the reaction is hindered, however, excessive use is acceptable.

It is advisable to add a phase transfer catalyst to the reaction system in order to increase the reaction rate, the conversion and the selectivity of the 9-isomer. The phase transfer catalysts used are quaternary ammonium salts having the general formula (VI):

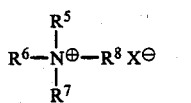
(VI)

wherein $R^5$, $R^6$ and $R^7$ are the same or different and each is an alkyl group having 1 to 18 carbon atoms, $R^8$ is an alkyl group having 1 to 10 carbon atoms or an aralkyl group having 7 to 12 carbon atoms, and X is hydroxyl group or halogen; polyethylene glycols or their alkyl ethers having the general formula (VII):

(VII)

wherein $R^9$ is hydrogen or an alkyl group having 1 to 4 carbon atoms and m is an integer of not less than 3; and diethylene glycol or its alkyl ethers having the general formula (VIII):

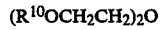
(VIII)

wherein $R^{10}$ is hydrogen or an alkyl group having 1 to 4 carbon atoms. Phosphonium salts and crown ethers which are generally used as phase transfer catalysts also can be used. From the industrial point of view, however, the above three kinds of catalysts and particularly, polyethylene glycols are preferable. The preferred examples of the phase transfer catalyst are trioctylmethylammonium chloride [$(n-C_8H_{17})_3N^{\oplus}CH_3Cl^{\ominus}$] out of the above quaternary ammonium salts, and polyethylene glycols or their alkyl ethers having a molecular weight of 500 to 2,000 out of the above polyethylene glycols.

The amount of phase transfer catalyst used varies depending upon the kind of $N^6$-substituted adenine and benzyl halide compound used for the reaction. Generally speaking, however, the amount is in the range of from 1 to 20% by mole of that of $N^6$-substituted adenine used, preferably from 5 to 15% by mole.

Any solvent can be used with no regard to the kind of phase transfer catalyst, only if it does not substantially dissolve the metal salt of $N^6$-substituted adenine and easily dissolves the benzyl halide compound. More specifically, it includes n-hexane, acetone, methyl ethyl ketone, methyl isobutyl ketone, hexamethylphosphoramide and toluene. The polyethylene glycol or its alkyl ether of the general formula (VII) and the diethylene glycol or its alkyl ether of the general formula (VIII) can be used not only as the phase transfer catalyst but also as the solvent. There are almost no other substances that can serve as the phase transfer catalyst and also as the solvent.

The use of the polyethylene glycol or diethylene glycol or their alkyl ether as the phase transfer catalyst and the solvent has a characteristic that the reaction temperature can be set freely. It is not possible to separate the polyethylene glycol or the diethylene glycol from the resulting disubstituted adenines by evaporation after the reaction. Accordingly, the reaction mixture is put into a large quantity of water to precipitate the desired product being insoluble in water in crystal form.

The reaction temperature varies depending on the kind of the solvent and the phase transfer catalyst used but usually ranges from 20° to 150° C. In particular, it is preferable to carry out the reaction under reflux. There is no particular limitation with respect to the reaction time. Preferably the reaction time is decided so that the starting material, $N^6$-substituted adenine is exhausted as completely as possible, because it is generally quite hard to separate the reaction product from the unchanged starting material, $N^6$-substituted adenine. The reaction time is usually from 2 to 50 hours.

The $N^6$-substituted adenines as a starting material can be produced readily by a known method such as the reaction of 6-chloropurine or 6-methylmercaptopurine with the corresponding amine.

However, the present inventors have found out a process for preparing a $N^6$-substituted adenine of the general formula (IV) in a high yield by reacting adenine with an aliphatic amine of the general formula (V).

The process is characterized by reacting adenine with an aliphatic amine of the general formula (V) at a temperature of 100° to 200° C.

In this process, adenine which is now available in a large quantity and at a low price because of the increasing demand in various fields and the advanced manufacturing technique of recent years is used as a starting material and the $N^6$-substituted adenines of the general formula (IV) are obtained by a one-step process wherein such adenine is reacted with an aliphatic amine of the general formula (V).

A process for preparing $N^6$-substituted adenines through reaction of adenine with primary amines is stated in Japanese Examined Pat. Publication No. 7955/1968. The invention of this literature is directed to a process for preparing substances which promote cell division of plants and animals, and also their growth. The working examples thereof are limited to the use of aralkyl amines such as benzylamine and furfurylamine, and higher alkylamines such as n-hexylamine as the primary amine, and do not include the use of lower aliphatic amines as given by the general formula (V). Besides the above literature, J. Am. Chem. Soc., Vol 82, 3971 (1960) and Japanese Examined Patent Publication No. 6954/1968 describe processes for preparing $N^6$-substituted adenines through amine exchange reaction of such type. None of these, however report the use of lower alkylamines.

The primary key point in the process of preparing $N^6$-substituted adenines in accordance with the present invention is the reaction temperature, which must be within the range of from 100° to 200° C., preferably from 150° to 180° C. As a matter of course, the reaction still proceeds to some extent even under 100° C. or over 200° C. but the yield is remarkably lowered, which fails to meet the object of the present invention.

Moreover, it is desirable to employ an acid catalyst to accelerate the reaction. Examples of the acid catalyst used include hydrogen halides such as hydrogen chloride and hydrogen bromide, mineral acids such as hydrochloric acid, sulfuric acid and nitric acid, organic sulfonic acids such as p-toluenesulfonic acid, and Lewis acids such as anhydrous aluminum chloride and zinc chloride. Salts of the aliphatic amine as one of the starting materials with mineral acid may also be used. Also used as the catalyst in place of such acid catalysts are metals and metallic ions which can form a complex salt with the aliphatic amine in situ in the reaction system, for example, Raney nickel and Raney cobalt. The catalyst is used in an amount of 1 to 10 moles per 1 mole of adenine.

It is preferable to use a solvent for smooth reaction, since the aliphatic amine given by the general formula (V) is gaseous under normal temperature or low boiling even when it is liquid. Water and lower alcohols having 1 to 4 carbon atoms are generally used as the solvent but any other solvents capable of dissolving the amine of the general formula (V) can be used with no particular limitation. The amount of solvent used is not limited if it is sufficient to ensure full agitation for the reaction.

The reaction is carried out in a sealed vessel. The aliphatic amine, the amount of which is 1 to 15 moles, preferably 5 to 10 moles, per 1 mole of adenine is absorbed into the solvent used or introduced directly into the sealed vessel. The reaction time is generally from 2 to 50 hours, though it varies depending upon the reaction temperature and the kind of solvent and catalyst used.

After completion of the reaction, the reaction mixture is taken out of the sealed vessel and the excess aliphatic amine and solvent are recovered by distillation under a reduced pressure. Water is added to the residue in an amount of about 10 times the volume of the residue to give a suspension. The suspension is adjusted to a pH value of not less than 11 with an alkali to dissolve the suspended material and the remaining insoluble material is filtered off. Then the aliphatic amine liberated is recovered by distillation under a reduced pressure. When an acid is added to the resulting solution to neutralize, a $N^6$-substituted adenine is precipitated. The precipitate is filtered and dried to give almost completely pure $N^6$-substituted adenine.

The crude $N^6$,9-disubstituted adenine obtained by the process of the present invention contains approximately 10 to 30 % by weight of a $N^6$,3-disubstituted adenine, though it differs more or less depending on the production conditions adopted. Such a crude $N^6$,9-disubstituted adenine is mixed with glacial acetic acid, the amount of which is 1.5 to 2.0 times the weight of the crude $N^6$,9-disubstituted adenine, and the mixture is dissolved by heating at a temperature of 90° to 95° C. Insoluble materials such as dust, if any, are removed by filtration. Then hot water is added in an amount of 5 to 10 times the volume of the solution to precipitate crystals. After cooling, the crystalline precipitate is filtered and washed first with an about 20% by weight solution of acetic acid in water and then with water. Since the obtained crystals are in the form of a salt with acetic acid, it is necessary to remove the acetic acid by suitable method. Vacuum drying at a temperature of 100° to 150° C. is a handy method to remove the acetic acid.

The purification method of the present invention is much easier in operation than the conventional decomposition method using sulfuric acid and the removing ratio of the 3-isomer is high. It is possible to lower the content of the 3-isomer in the crystal obtained below 1% by weight by single purification operation.

The present invention is more particularly described and explained by means of the following Examples. These Examples are intended to illustrate the invention and not be construed to limit the scope of the invention. It is to be understood that various changes and modifications may be made in the invention without departing from the spirit and scope thereof.

In Examples, the purity of the intermediate and the final product and the content of the 3-isomer in the final product were measured by high performance liquid chromatography (HPLC) using a cation exchange column.

EXAMPLE 1

Into 350 ml. of ethanol was absorbed 89 g. (2.85 moles) of methylamine. Into another 350 ml. of ethanol was absorbed 25.5 g. (0.7 mole) of anhydrous hydrogen chloride. The resulting two solutions were put into an autoclave together with 67.5 g. (0.5 mole) of adenine and the reaction was carried out at 160° C. for 24 hours. The internal pressure was 18 kg./cm$^2$. After completing the reaction, the ethanol was removed by distillation and 700 ml. of water and then 140 g. (0.7 mole) of a 20% by weight aqueous solution of sodium hydroxide were added, and then the evolved methylamine was removed by distillation under a reduced pressure at 50° C. for one hour. The resultant was neutralized with sulfuric acid and the crystalline precipitate was filtered and dried at 70° C. for 15 hours to give 73 g. of $N^6$-methyladenine. The purity was 96.0% by weight and the yield was 94%.

A part of the crude $N^6$-methyladenine was recrystallized from a large quantity of ethanol to give a specimen for analysis.

Melting point: 313° to 315° C.

Elemental analysis for $C_6H_7N_5$: Calcd. (%): C 48.31, H 4.73, N 46.96 Found. (%): C 48.27, H 4.71, N 46.99.

UV absorption spectrum $\lambda_{max}^{0.1N\ HCl}$: 267 nm.

The infrared absorption spectrum completely coincided with the spectrum of the specimen of $N^6$-methyladenine prepared from 6-chloropurine and methylamine by a known method.

EXAMPLE 2

Into 100 ml. of ethanol was absorbed 31.8 g. (1.02 moles) of methylamine. Into another 100 ml. of ethanol was absorbed 9.1 g. (0.25 mole) of anhydrous hydrogen chloride. The resulting two solutions were put into an autoclave together with 13.5 g. (0.1 mole) of adenine and reaction was carried out with agitating at 200° C. for 4.5 hours. The internal pressure was 38 kg./cm$^2$. After completing the reaction, the ethanol was removed by distillation, and 140 ml. of water and then 50 g. (0.25 mole) of a 20% by weight aqueous solution of sodium hydroxide were added. The resultant was then treated in the same manner as in Example 1 to give 12.0 g. of $N^6$-methyladenine. The purity was 94.7% by weight and the yield was 76%.

EXAMPLE 3

The same procedures as in Example 2 except that 16.5 g. (0.53 mole) of methylamine and 6 g. ( 0.16 mole) of anhydrous hydrogen chloride were used were repeated to give 7 g. of $N^6$-methyladenine. The purity was 91.0% by weight and yield was 43%.

EXAMPLE 4 to 6

The same procedures as in Example 3 except that the reaction temperature and the reaction time were changed to those shown Table 1 were repeated to give $N^6$-methyladenine. The results are also shown in Table 1 together with the results of Example 3.

TABLE 1

| Ex. No. | Reaction condition | | Result | | |
|---|---|---|---|---|---|
| | Temp. (°C.) | Time (hr.) | Amount (g.) | Purity (% by weight) | Yield (%) |
| 3 | 200 | 4.5 | 7 | 91.0 | 43 |
| 4 | 150 | 4.5 | 5.6 | 76.1 | 29 |
| 5 | 150 | 20 | 11.6 | 95.8 | 75 |
| 6 | 130 | 30 | 10.6 | 47.6 | 34 |

EXAMPLE 7

Into 100 ml. of water was absorbed 20.8 g. (0.67 mole) of methylamine. To 14.2 g. (0.14 mole) of a 36% by weight hydrochloric acid was added 91 ml. of water. The resulting two solutions were put into an autoclave together with 13.5 g. (0.1 mole) of adenine and the reaction was carried out at 150° C. for 7 hours. The internal pressure was 3 kg./cm². After completing the reaction, 28 g. (0.14 mole) of a 20% aqueous solution of sodium hydroxide was added and the evolved methylamine was removed by distillation under a reduced pressure at 50° C. for one hour. The resultant was then treated in the same manner as in Example 1 to give 9.6 g. of $N^6$-methyladenine. The purity was 30.0% by weight and the yield was 19%.

EXAMPLE 8 to 12

The same procedures as in Example 4 except that various kinds of acid catalysts as shown in Table 2 were used instead of anhydrous hydrogen chloride were repeated to give $N^6$-methylamine. The results are also shown in Table 2 together with the results of Example 4.

TABLE 2

| Ex. No. | Acid catalyst | Conc. of acid used (% by weight) | Results | | |
|---|---|---|---|---|---|
| | | | Amount (g.) | Purity (% by weight) | Yield (%) |
| 4 | Hydrogen chloride | — | 5.6 | 76.1 | 29 |
| 8 | Sulfuric acid | 97 | 3.0 | 13.6 | 3 |
| 9 | Nitric acid | 60 | 9.8 | 38.2 | 25 |
| 10 | p-Toluene-sulfonic acid | — | 9.2 | 39.9 | 25 |
| 11 | Anhydrous aluminum chloride | — | 11.3 | 38.4 | 29 |
| 12 | Zinc chloride | — | 10.5 | 28.6 | 20 |

EXAMPLES 13 and 14

The same procedures as in Example 8 except that the reaction temperature was changed to those shown in Table 3 were repeated to give $N^6$-methyladenine. The results are also shown in Table 3 together with the results of Example 8.

TABLE 3

| Ex. No. | Reaction temp. (°C.) | Results | | |
|---|---|---|---|---|
| | | Amount (g.) | Purity (% by weight) | Yield (%) |
| 8 | 150 | 3.0 | 13.6 | 3 |
| 13 | 175 | 14.5 | 33.2 | 32 |
| 14 | 200 | 3.7 | 82.7 | 21 |

EXAMPLE 15

A solution prepared by absorbing 18.9 g. (0.61 mole) of methylamine into 100 ml. of ethanol, a catalyst prepared by developing 1.35 g. of Raney nickel containing 8% by weight of nickel, 100 ml. of ethanol and 13.5 g. (0.1 mole) of adenine were placed into an autoclave and the reaction was carried out at 150° C. for 4.5 hours. After completing the reaction, the ethanol was removed by distillation, and 600 ml. of water and then 15 g. of a 20% by weight aqueous solution of sodium hydroxide were added. The resultant was heated under reflux to dissolve the reaction product and the insoluble material was filtered off under heating. After cooling, the filtrate was neutralized with sulfuric acid to precipitate crystals. The precipitate was filtered, washed with water and dried at 70° C. for 15 hours to give 14.2 g. of $N^6$-methyladenine The purity was 15.5% by weight and the yield was 15%.

EXAMPLE 16

To 350 ml. of ethanol was added 147.8 g. (2.5 moles) of n-propylamine. Into another 350 ml. of ethanol was absorbed 25.5 g. (0.7 mole) of anhydrous hydrogen chloride. The resulting two solutions were put into an autoclave together with 67.5 g. (0.5 mole) of adenine and the reaction was carried out at 160° C. for 24 hours. After completing the reaction, the excess n-propylamine and ethanol were removed by distillation, and 700 ml. of water and then 140 g. (0.7 mole) of a 20% by weight of aqueous solution of sodium hydroxide were added to the residue and the evolved n-propylamine was evaporated under a reduced pressure at 50° C. The residual solution was neutralized with a 49 % by weight sulfuric acid, and the precipitated crystals were filtered and dried at 70° C. for 15 hours to obtain 85.7 g. of a crude $N^6$-n-propyladenine. The purity was 97.5% by weight and the yield was 94.3%. The infrared absorption spectrum of the product coincided with the spectrum of the specimen of $N^6$-n-propyladenine prepared from 6-chloropurine and n-propylamine by a known method.

EXAMPLE 17

The same procedures as in Example 1 except that 121.7 g. (2.7 moles) of dimethylamine was used instead of methylamine were repeated to give 75.9 g. of a crude $N^6$-dimethyladenine. The purity was 96.8% by weight and the yield was 95.9%. The infrared absorption spectrum of the product coincided completely with the spectrum of the specimen of $N^6$-dimethyladenine prepared from 6-chloropurine and dimethylamine by a known method.

EXAMPLE 18

To 100 ml. of acetone were added 6.5 g. (0.0435 mole) of $N^6$-methyladenine which had a purity of 99.8% by weight and was prepared by recrystallizing the product obtained in Example 1 from ethanol, and 3.5 g. (0.0435 mole) of a 50% by weight aqueous solution of sodium hydroxide. The mixture was heated under reflux for 1.5 hours. A solution prepared by dissolving 7.8 g. (0.0435 mole) of 2-chloro-6-fluorobenzyl chloride and 1.17 g. (0.0026 mole) of a 90% by weight trioctylmethyl ammonium chloride as a phase transfer catalyst into 17 ml. of acetone was added thereto and the resultant was heated under reflux for 6 hours. After completing the reaction, the acetone was removed by distillation and the resulting powdery residue was taken out and dried at 70° C. for 15 hours to give 12.4 g. of a crude 9-(2-chloro-6-fluorobenzyl)-$N^6$-methyladenine in crystal form. The purity was 79.4% by weight and the content of the 3-isomer was 20.6% by weight.

EXAMPLES 19 to 21

The same procedures as in Example 18 except that various quaternary ammonium salts shown in Table 4 were used as a phase transfer catalyst were repeated to give 9-(2-chloro-6-fluorobenzyl)-N6-methyladenine. The results are also shown in Table 4 together with the results of Example 18.

TABLE 4

| | | Product | | |
|---|---|---|---|---|
| Ex. No. | Quaternary ammonium salt | Raw yield (g.) | Purity (% by weight) | Content of 3-isomer (% by weight) |
| 18 | $(n-C_8H_{17})_3N^{\oplus}CH_3Cl^{\ominus}$ | 12.4 | 79.4 | 20.6 |
| 19 | $(n-C_4H_9)_4N^{\oplus}Br^{\ominus}$ | 11.6 | 46.5 | 30.9 |
| 20 | $(C_2H_5)_3N^{\oplus}CH_2C_6H_5Cl^{\ominus}$ | 12.5 | 27.9 | 31.4 |
| 21 | $CH_3-\langle\text{pyridinium}\rangle-N^{\oplus}C_{12}H_{25}Cl^{\ominus}$ | 13.3 | 34.8 | 35.1 |

EXAMPLE 22

The same procedures as in Example 18 except that 8.5 g. (0.0435 mole) of 2,6-dichlorobenzyl chloride was used in place of 2-chloro-6-fluorobenzyl chloride were repeated to give 16.07 g. of a crude 9-(2,6-dichlorobenzyl)-$N^6$-methyladenine in crystal form. The purity was 61.7% by weight and the content of the 3-isomer was 32.2% by weight.

EXAMPLE 23

The same procedures as in Example 18 except that 5.5 g. (0.0435 mole) of benzyl chloride was used in place of 2-chloro-6-fluorobenzyl chloride were repeated to give 11.86 g. of a crude 9-benzyl-$N^6$-methyladenine in crystal form. The purity was 41.7% by weight.

EXAMPLES 24 to 26

The same procedures as in Example 18 except that various kinds of $N^6$-substituted adenines shown in Table 5 were used instead of $N^6$-methyladenine were repeated to give $N^6$,9-disubstituted adenines. The results are also shown in Table 5 together with the results of Example 18.

TABLE 5

| | | Product | | |
|---|---|---|---|---|
| Ex. No. | $N^6$—Substituted adenine | Raw yield (g.) | Purity (% by weight) | Content of 3-isomer (% by) weight) |
| 18 | $N^6$—Methyl-adenine | 12.4 | 79.4 | 20.6 |
| 24 | $N^6$—n-Propyl-adenie | 17.4 | 63.9 | 24.5 |
| 25 | $N^6$—Benzyl-adenine | 16.7 | 19.5 | 1.7 |
| 26 | $N^6,N^6$—Dimethyl-adenine | 14.6 | 58.6 | 10.8 |

Example 27

To 100 ml. of acetone were added 6.5 g. (0.0435 mole) of $N^6$-methyladenine and 3.5 g. (0.0435 mole) of a 50% by weight aqueous solution of sodium hydroxide. The mixture was heated under reflux for 1.5 hours. To the suspension was added a solution prepared by dissolving 7.8 g. (0.0435 mole) of 2-chloro-6-fluorobenzyl chloride and 2.61 g. (0.00435 mole) of polyethylene glycol (average molecular weight: 600) into 20 ml. of acetone. The mixture was heated under reflux for 6 hours. After evaporating the resulting acetone, the powdery residue was taken out and dried at 70° C. for 20 hours to give 15.79 g. of a crude 9-(2-chloro-6-fluorobenzyl)-$N^6$-methyladenine in crystal form. The purity was 67.5% by weight and the content of the 3-isomer was 6.7% by weight.

EXAMPLES 28 to 33

The same procedures as in Example 27 except that polyethylene glycols having different molecular weights, their dialkyl ethers and diethylene glycol dialkyl ether as shown in Table 6 were used as a phase transfer catalyst were repeated to give 9-(2-chloro-6-fluorobenzyl)-$N^6$-methyladenine. The results are also shown in Table 6 together with the results of Example 27.

TABLE 6

| | | Product | | |
|---|---|---|---|---|
| Ex. No. | Phase transfer catalyst | Raw yield (g.) | Purity (% by weight) | Content of 3-isomer (% by weight) |
| 27 | Polyethylene glycol-600 | 15.79 | 67.5 | 6.7 |

TABLE 6-continued

| Ex. No. | Phase transfer catalyst | Raw yield (g.) | Product Purity (% by weight) | Content of 3-isomer (% by weight) |
|---|---|---|---|---|
| 28 | Polyethylene glycol-400 | 14.88 | 60.2 | 8.5 |
| 29 | Polyethylene glycol-1000 | 15.93 | 66.8 | 6.8 |
| 30 | Polyethylene glycol-600 diethyl ether | 15.25 | 60.3 | 9.2 |
| 31 | Polyethylene glycol-600 dipropyl ether | 15.04 | 61.3 | 9.5 |
| 32 | Polyethylene glycol-400 dibutyl ether | 12.86 | 62.8 | 8.2 |
| 33 | Diethylene glycol diethyl ether | 13.25 | 52.6 | 8.4 |

EXAMPLE 34

To 40 ml. of water were added 40 g. (purity: 92.6% by weight) of $N^6$-methyladenine and then 20.8 g. of a 48% by weight aqueous solution of sodium hydroxide. The crystals of $N^6$-methyladenine were dissolved by heating. After evaporating the water under a reduced pressure, the residue was subjected to vacuum drying at 75° C. for 16 hours to give $N^6$-methyladenine sodium salt. The moisture content of the obtained $N^6$-methyladenine sodium salt was 6.14% by weight (by Karl Fisher method).

Into 120 ml. of polyethylene glycol (average molecular weight: 600) was suspended 7.4 g. of the above $N^6$-methyladenine sodium salt. To the suspension was added 7.8 g. of 2-chloro-6-fluorobenzyl chloride. The mixture was heated at 60° C. for 6 hours. After cooling, the reaction mixture was poured into 1,000 ml. of water and the resultant was fully agitated. The resulting precipitate was filtered and dried at 70° C. for 15 hours to give 12.4 g. of a crude 9-(2-chloro-6-fluorobenzyl)-N-$^6$-methyladenine. The purity was 86.9% by weight and the content of the 3-isomer was 11.4% by weight.

EXAMPLE 35

The same procedures as in Example 34 except that diethylene glycol dimethyl ether was used as the solvent and phase transfer catalyst instead of polyethylene glycol (average molecular weight: 600) were repeated to give 12.1 g. of a crude 9-(2-chloro-6-fluorobenzyl)-$N^6$-methyladenine. The purity was 51.1% by weight and the content of the 3-isomer was 8.7% by weight.

EXAMPLE 36

To 100 ml. of acetone was suspended 7.4 g. of $N^6$-methyladenine sodium salt prepared in Example 34. The suspension was mixed with a mixture of 7.8 g. of 2-chloro-6-fluorobenzyl chloride, 2.61 g. of polyethylene glycol (average molecular weight: 1,000) and 20 ml. of acetone and was heated under reflux for 6 hours. After the acetone was evaporated, the residue was taken out and dried at 70° C. for 15 hours to give 15.5 g. of a crude 9-(2-chloro-6-fluorobenzyl)-$N^6$-methyladenine. The purity was 75.1% by weight and the content of the 3-isomer was 6.0% by weight.

EXAMPLE 37

The same procedures as in Example 27 except that a 50% by weight aqueous solution of potassium hydroxide was used in place of the 50% by weight aqueous solution of sodium hydroxide were repeated to give 18.2 g. of a crude 9-(2-chloro-6-fluorobenzyl)-$N^6$-methyladenine. The purity was 55.9% by weight and the content of the 3-isomer was 8.3% by weight.

EXAMPLE 38

To 100 ml. of water were added 6.5 g. of $N^6$-methyladenine (purity: 99.8% by weight) and 7.46 g. of barium hydroxide 8 hydrate. The mixture is heated to dissolve the solids and the resulting solution was concentrated to dryness. The obtained residue was dried at 80° C. for 16 hours to give 14.97 g. of $N^6$-methyladenine barium salt.

Into 120 ml. of acetone were added 14.97 g. of the above $N^6$-methyladenine barium salt, 7.8 g. of 2-chloro-6-fluorobenzyl chloride and 2.61 g. of polyethylene glycol (average molecular weight: 1,000). The mixture was heated under reflux for 6 hours. After evaporating the acetone, the residue was dried at 70° C. for 15 hours to give 22.6 g. of a crude 9-(2-chloro-6-fluorobenzyl)-$N^6$-methyladenine. The purity was 50.2% by weight and the content of the 3-isomer was 4.6% by weight.

EXAMPLE 39

(1) Alkylation

To 744 ml. of acetone were added 50 g. of $N^6$-methyladenine (purity: 92.6% by weight) and 24.9 g. of a 50% by weight aqueous solution of sodium hydroxide. The mixture was heated under reflux for 3 hours. To the mixture was added a solution prepared by dissolving 55.9 g. of 2-chloro-6-fluorobenzyl chloride and 8.4 g. of tri-n-octylmethylammonium chloride (90% by weight aqueous solution) into 124 ml. of acetone. The resultant was heated under reflux for 6 hours. After completing the reaction, the acetone was recovered by distillation and 750 ml. of 0.1N sodium hydroxide was added to the residue. The resultant was agitated for about 15 minutes at a room temperature. The resulting precipitate was filtered and repeatedly washed with water until the filtrate became neutral. The obtained crystals were dried in a hot air drier at 70° C. for 20 hours to give 88.3 g. of a crude 9-(2-chloro-6-fluorobenzyl)-$N^6$-methyladenine. The yield was 98 %, and the purity was 76.6% by weight and the content of the 3-isomer was 23.4% by weight.

(2) Purification 88.3 grams of the crude product was added to 160 ml. of glacial acetic acid and heated at 90° to 95° C. to dissolve the crystals. Then a slight amount of impurity was filtered off under heating, and 720 ml. of hot water (about 90° C.) was added to the filtrate to precipitate crystals. After agitating at 90° to 95° C. for 5 minutes, the mixture was cooled and the precipitated crystals were recovered by filtration. The crystals were washed with 90 ml. of a 20% by weight solution of acetic acid in water and then with 140 ml. portions of water three times. The obtained crystals were dried at 130° C./2 mmHg. for 10 hours to give 61.4 g. of a pure 9-(2-chloro-6-fluorobenzyl)-N⁶-methyladenine. The yield was 68% (from N⁶-methyladenine), and the purity was 99.83% by weight and the content of the 3-isomer was 0.17% by weight. The yield in purification step with respect to the 9-isomer is 90.6%.

To lower the content of the 3-isomer to less than 100 p.p.m., the same purification procedure as above was repeated again. In the obtained product, the 3-isomer was not detected by HPLC.

EXAMPLE 40

(1) Alkylation

Employing N⁶,N⁶-dimethyladenine prepared in Example 17 and 2-chloro-6-fluorobenzyl chloride, the same procedures as in Example 39, (1) were repeated to give a crude 9-(2-chloro-6-fluorobenzyl)-N⁶, N⁶-dimethyladenine, in which the purity was 73.1% by weight and the content of the 3-isomer was 26.9% by weight.

(2) Purification

To 21 ml. of glacial acetic acid was added 10.9 g. of the above crude product, and the mixture was heated at 90° to 95° C. to dissolve the crystals, followed by addition of 90 ml. of hot water to precipitate crystals. After cooling, the crystals were filtered, washed with 20 ml. of a 20 % by weight solution of acetic acid in water and then with 20 ml. portions of water 3 times, and vacuum-dried at 130° C./5 mmHg. for 20 hours to give 5.2 g. of a pure 9-(2-chloro-6-fluorobenzyl)-N⁶,N⁶-dimethyladenine. The yield was 48% (from N⁶, N⁶dimethyladenine) and the purity is 99.5% by weight and the content of the 3-isomer was 0.5% by weight. The yield in purification step with respect to the 9-isomer was 64.9%.

EXAMPLE 41

(1) Alkylation

Exploying N⁶-n-propyladenine prepared in Example 16 and 2,6-dichlorobenzyl chloride, the same procedures as in Example 39, (1) were repeated to give a crude 9-(2,6-dichlorobenzyl)-N⁶-n-propyladenine, in which the purity was 72.6% by weight and the content of the 3-isomer was 27.4% by weight.

(2) Purification

To 8 ml. of glacial acetic acid was added 4.0 g. of the above crude product, and the mixture was heated at 90° to 95° C. to dissolve the crystals, followed by addition of 32 ml. of hot water to precipitate crystals. After cooling, the crystals were filtered, washed with 4 ml. of a 20% by weight solution of acetic acid in water and then with 6 ml. portions of water 3 times, and vacuum-dried at 130° C./5 mmHg. for 20 hours to give 1.7 g. of a pure 9-(2,6-dichlorobenzyl)-N⁶-n-propyladenine The yield was 42% (from N⁶-n-propyladenine) and the purity was 94.4% by weight and the content of the 3-isomer was 5.6% by weight. The yield in purification step with respect to the 9-isomer was 55.3%.

EXAMPLE 42

(1) Alkylation

The same procedures as in Example 39, (1) except that 18.6 g. of polyethylene glycol (average molecular weight: 1,000) was used in place of 8.4 g. of tri-n-octyl-methylammonium chloride were repeated to give 89.0 g. of a crude 9-(2-chloro-6-fluorobenzyl)-N⁶-methyladenine. The yield was 98.3% and the purity was 81.0% by weight and the content of the 3-isomer was 19.0% by weight.

(2) Purification

Employing 89.0 g. of the above crude product, the purification was performed in the same manner as in Example 39, (2) to give 70.2 g. of a pure 9-(2-chloro-6-fluorobenzyl)-N⁶-methyladenine. The yield was 77.5% (from N⁶-methyladenine), and the purity was 99.97% by weight and the content of the 3-isomer was 0.03% by weight. The yield in purification step with respect to the 9-isomer was 97.3%.

What is claimed is:

1. A process for preparing a $N^6,9$-disubstituted adenine having the general formula (I):

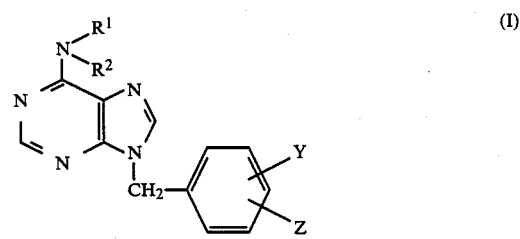

wherein $R^1$ is hydrogen, a lower alkyl group having 1 to 4 carbon atoms, benzyl group or furfuryl group, $R^2$ is a lower alkyl group having 1 to 4 carbon atoms, benzyl group or furfuryl group, Y and Z are the same or different and each is hydrogen, chlorine, bromine or fluorine, which comprises reacting a metal salt of $N^6$-substituted adenine having the general formula (II):

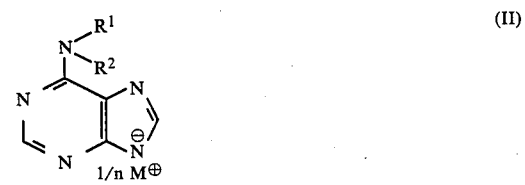

wherein $R^1$ and $R^2$ are the same as defined above, M is an alkali metal or an alkaline earth metal and n is an integer of 1 or 2, with a benzyl halide compound having the general formula (III):

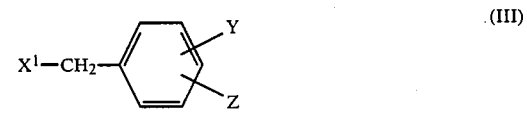

wherein Y and Z are the same as defined above, and $X^1$ is chlorine or bormine, in the presence of a phase transfer catalyst selected from the group consisting of polyethylene glycol or its alkyl ether having the general formula (VII):

$$R^9O(CH_2CH_2O)_mR^9 \qquad (VII)$$

wherein $R^9$ is hydrogen or an alkyl group having 1 to 4 carbon atoms and m is an integer of not less than 3; and diethylene glycol or its alkyl ether having the general formula (VIII):

$$(R^{10}OCH_2CH_2)_2O \qquad (VIII)$$

wherein $R^{10}$ is hydrogen or an alkyl group having 1 to 4 carbon atoms, whereby formation of the 3-isomer is suppressed.

2. The process of claim 1, in which the metal salt of the general formula (II) is formed by reacting a $N^6$-substituted adenine having the general formula (II'):

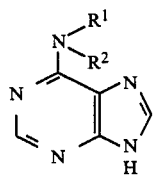
(II')

wherein $R^1$ and $R^2$ are the same as defined above, with a strongly basic compound of an alkali metal or an alkaline earth metal in a solvent, and without isolating the formed metal salt from the reaction mixture, the metal salt is reacted with the benzyl halide compound of the general formula (III).

3. The process of claim 1, in which the reaction is carried out in the presence of the polyethylene glycol or its alkyl ether of the general formula (VII) which serves as a phase transfer catalyst and a reaction solvent.

4. The process of claim 1, in which the reaction is carried out in the presence of diethylene glycol or its alkyl ether of the general formula (VIII) which serves as a phase transfer catalyst and a reaction solvent.

5. The process of claim 1, in which the metal salt of the general formula (II) is a metal salt derived rom a $N^6$-substituted adenine having the general formula (IV):

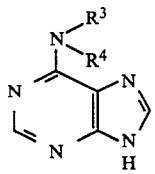
(IV)

wherein $R^3$ is hydrogen or a lower alkyl group having 1 to 4 carbon atoms, and $R^4$ is a lower alkyl group having 1 to 4 carbon atoms, which is prepared by reacting adenine with an aliphatic amine having the general formula (V):

(V)

wherein $R^3$ and $R^4$ are the same as defined above, at a temperature of 100° to 200° C.

6. The process of claim 5, in which the reaction of adenine with the aliphatic amine of the general formula (V) is carried out in the presence of a catalyst selected from the group consisting of a hydrogen halide; a mineral acid; an organic sulfonic acid; a Lewis acid; and a metal or metal salt capable of forming a complex ion with the aliphatic amine of the general formula (V) in situ in the reaction.

7. The process of claim 6, in which the reaction is carried out in a solvent capable of dissolving the aliphatic amine of the general formula (V).

8. The process of claim 7, in which the solvent is water or a lower alcohol having 1 to 4 carbon atoms.

9. The process of claim 1, in which the obtained reaction product is dissolved in glacial acetic acid by heating and hot water is added to the resulting solution to precipitate selectively the $N^6$,9disubstituted adenine of the general formula (I).

* * * * *